US00PP10171P

United States Patent [19]

Trees

[11] Patent Number: Plant 10,171

[45] Date of Patent: Dec. 30, 1997

[54] NEW GUINEA IMPATIENS NAMED 'BFP-698 CHERRY'

[75] Inventor: Scott C. Trees, Arroyo Grande, Calif.

[73] Assignee: Ball Horticulture Company, West Chicago, Ill.

[21] Appl. No.: 718,702

[22] Filed: Sep. 27, 1996

[51] Int. Cl.[6] ..... A01H 5/00

[52] U.S. Cl. ..... Plt./87.6

[58] Field of Search ..... Plt./87.4

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'BFP-698 Cherry' is provided. This new cultivar was the result of a controlled breeding program wherein a plant designated 6801-4 (non-patented in the United States) was pollinated by a plant designated 307 (non-patented in the United States). The new cultivar forms large bright cherry red flowers that display an iridescent appearance. The foliage is glossy dark green in coloration. An attractive compact upright mounted growth habit is exhibited. The new cultivar can be readily distinguished from the 'BFP-467 Cherry Red' cultivar (U.S. Plant Pat. No. 9,520).

1 Drawing Sheet

SUMMARY OF THE INVENTION

The present invention comprises a new and distinctive Impatiens plant, botanically known as New Guinea Impatiens, and hereinafter is referred to by the cultivar name 'BFP-698 Cherry'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was a plant designated 6801-4 (non-patented in the United States) which exhibits medium lavender flowers, dark green foliage, and a vigorous growth habit. The male parent (i.e., the pollen parent) was a plant designated 307 (non-patented in the United States) which exhibits red flowers, dark green foliage, and a compact growth habit. The parentage of the new cultivar can be summarized as follows:

6804-4×307.

The seeds resulting from the above pollination were sown and plantlets were obtained which were physically and biologically different from each other. Selective study resulted in the identification of a single plant of the new cultivar. This plant initially was designated BFP-698.

It was found that the new cultivar of the present invention:

(a) exhibits attractive large bright cherry red flowers,
(b) forms glossy dark green foliage,
(c) exhibits a good basal branching character, and
(d) exhibits a compact upright growth habit.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'BFP-698 Cherry' cultivar has not been observed under all possible environmental conditions to date. Accordingly, it is possible that the phenotype may vary somewhat with variations in the environment, such as temperature, light intensity, and day length.

When the new cultivar of the present invention is compared to the 'BFP-467 Cherry Red' cultivar (U.S. Plant Pat. No. 9,520), it is found that the new cultivar exhibits slightly larger flowers, flower petals that are a lighter cherry red coloration, darker green foliage, and a more compact growth habit.

Plants of the new cultivar are marketed under the Celebrette trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein in The R.H.S. Colour Chart of The Royal Horticultural Society, London, England. The plants were produced from cuttings taken stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced during the summer and the longer times during the winter.

*Rooting habit.*—Fibrous, and branching.

Plant description:

*Form.*—Basal branching.

*Habit of growth.*—Medium upright, and mounded. A mature plant commonly measures approximately 5.5 to 6 cm. in height and approximately 9 to 11 cm. in width. This compares to a height of approximately 9 to 11 cm. and width of approximately 24 to 26 cm. for the 'BFP-467 Cherry Red' cultivar.

*Foliage.*—The configuration is elliptic with an acuminate apex and an accuminate base. The mature leaves of the new cultivar measure approximately 8 to 8.8 cm. in length × approximately 2.3 to 3 cm. in maximal width compared to approximately 10 to 11 cm. in length × approximately 3.7 to 4.2 cm. in maximal width for the 'BFP-467 Cherry Red' cultivar. The leaf margins are serrate (as illustrated). The mature foliage of new cultivar is Green Group 139A (adaxial) and Yellow-Green Group 148B (abaxial). This compares to Green Group 137B (adaxial) and Green Group 138B (abaxial) for the 'BFP-467 Cherry Red' cultivar. The stem coloration is Red Group 53B. This compares to Green Group 143C with an area of Greyed-Purple Group 185A at the nodes for the 'BFP-467 Cherry Red' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—Between Red Group 45A and Red Group 53C (adaxial), and between Red Group 45C and Red Group 53D (abaxial). The adaxial coloration is closest to Red Group 53C, but lighter and brighter. This compares to Red Group 46A (adaxial) and Red Group 46D (abaxial) for the 'BFP-467 Cherry Red' cultivar.

*Quantity of flowers.*—Approximately 4 to 6 per axil compared to approximately 3 to 4 per axil for the 'BFP-467 Cherry Red' cultivar.

*Number of petals.*—Five and overlapping.

*Petal shape.*—Heart-shaped, the upper three petals tend to have broader bases than the lower two petals.

*Flower size.*—Approximately 6.2 to 6.7 cm. in length and approximately 6.2 to 6.7 cm. in width. This can be compared to approximately 6.0 to 6.7 cm. in length and approximately 6.0 to 6.5 cm. in width for the 'BFP-467 Cherry Red' cultivar.

*Flower buds.*—Ellipsoidal in configuration, and generally covered with three sepals plus two rudimentary sepals fused into the under surface of the superior petal. A spur originating from the base of the inferior sepal is approximately 4 to 4.3 cm. in length on fully opened flowers which can be compared to approximately 4.9 to 5.5 cm. for the spur of the 'BFP-467 Cherry Red' cultivar.

*Reproductive organs.*—The stamens are Red Group 42A. The anthers tend to be fused together forming one organ that surrounds the pistil. Commonly the anthers shed pollen prior to the stigma becoming receptive. The pollen coloration in Yellow-Orange Group 15D and the ovary coloration is Yellow-Green Group 146B. This can be compared to a stamen coloration of Orange-Red Group 34A, a pollen coloration of Yellow Group 11D, and an ovary coloration of Yellow-Green Group 144C for the 'BFP-467 Cherry Red' cultivar.

I claim:

1. A new and distinct cultivar of New Guinea Impatiens plant named 'BFP-698 Cherry', substantially as herein shown and described, which:

(a) exhibits attractive large bright cherry red flowers,
(b) forms glossy dark green foliage,
(c) exhibits a good basal branching character, and
(d) exhibits a compact upright growth habit.

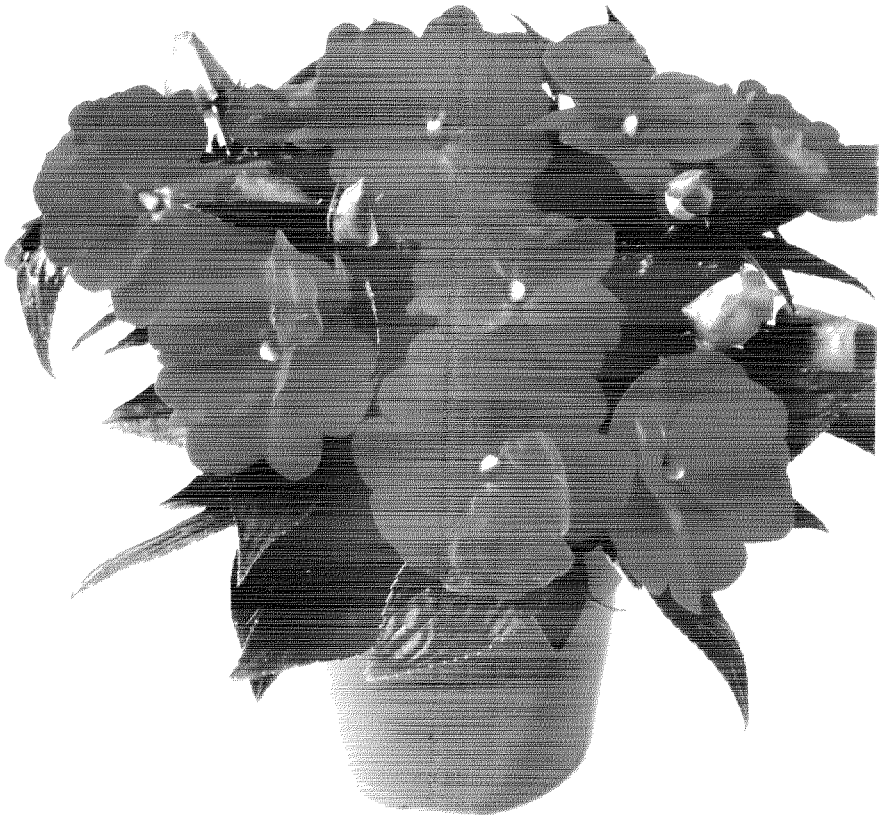

* * * * *